(12) United States Patent
Riley et al.

(10) Patent No.: US 6,228,136 B1
(45) Date of Patent: May 8, 2001

(54) CYANOBACTERIAL INOCULANTS FOR LAND RECLAMATION

(75) Inventors: Michael A. Riley, Towson, MD (US); Michael J. Orr, Orlando, FL (US); Jeffrey R. Johansen, Cleveland Heights, OH (US)

(73) Assignee: Engineering Technology, Incorporated, Orlando, FL (US)

( * ) Notice: Subject to any disclaimer, the term of this patent is extended or adjusted under 35 U.S.C. 154(b) by 0 days.

(21) Appl. No.: 09/245,032

(22) Filed: Feb. 4, 1999

(51) Int. Cl.⁷ .............................. C05F 11/08; A01G 7/00; C12N 1/12
(52) U.S. Cl. ................ 71/6; 71/7; 47/1.4; 47/48.5; 435/170; 435/177; 504/117
(58) Field of Search ................................. 435/170, 177; 47/48.5, 1.4; 504/117; 71/6, 7

(56) References Cited

U.S. PATENT DOCUMENTS

| | | |
|---|---|---|
| Re. 34,670 | 7/1994 | Williams et al. . |
| 3,898,132 | 8/1975 | Hettrick . |
| 3,969,844 | 7/1976 | Fogel et al. . |
| 4,001,480 | 1/1977 | Shank . |
| 4,434,231 | 2/1984 | Jung . |
| 4,649,110 | 3/1987 | Shilo et al. . |
| 4,774,186 | 9/1988 | Schaefer, Jr. et al. . |
| 4,879,232 | 11/1989 | MacDonald et al. . |
| 4,921,803 | 5/1990 | Nohr . |
| 4,950,601 | 8/1990 | MacDonald et al. . |
| 4,981,798 | 1/1991 | Kamakura et al. . |
| 5,163,931 | 11/1992 | Aldrett . |
| 5,174,807 | 12/1992 | MacDonald . |
| 5,300,127 | 4/1994 | Williams . |
| 5,441,877 | 8/1995 | Chiaffredo et al. . |
| 5,443,845 | 8/1995 | Felix . |
| 5,484,464 | 1/1996 | Gleddie et al. . |
| 5,522,985 | 6/1996 | Bender et al. . |
| 5,580,192 | 12/1996 | Ogawa et al. . |
| 5,593,883 | 1/1997 | Cano et al. . |
| 5,614,097 | 3/1997 | Bender et al. . |
| 6,033,559 * | 3/2000 | Bender et al. ........................ 435/177 |

* cited by examiner

Primary Examiner—Herbert J. Lilling
(74) Attorney, Agent, or Firm—Alan G. Towner; Eckert Seamans Cherin & Mellott, LLC (57) ABSTRACT

Materials inoculated with cyanobacteria are used to reclaim land. Methods and apparatus for making and disseminating cyanobacteria inoculants are disclosed. A thin-film growth method may be used to grow the cyanobacteria directly on a substrate material. Alternatively, the cyanobacteria may be grown separately, followed by application to the substrate material. Pieces of the inoculated substrate material are disseminated on soil. Upon contact with water, the cyanobacteria transform from a dormant stage to an active stage, and act to bind particles of the soil together.

21 Claims, 6 Drawing Sheets

Filamentous cyanobacteria grown on hemp.

FIG. 7

Cyanobacteria on fabric from soil sample.

FIG. 8

Cyanobacteria on fabric from soil sample.

Viability test 3 results

FIG. 12

CYANOBACTERIAL INOCULANTS FOR LAND RECLAMATION

FIELD OF THE INVENTION

The present invention relates to the reclamation of land, and more particularly relates to methods and apparatus for making and disseminating cyanobacterial inoculants for the reclamation of arid lands and the like.

BACKGROUND INFORMATION

Arid lands are subjected to environmental extremes that can lead to permanent damage of their top soil layer. High winds, high temperature and very low water content permit the rapid granulation of topsoil, leading to its rapid erosion. In some areas, military or recreational vehicle traffic causes additional erosion. The remaining subsurface offers little to flora and fauna for life support. Methods that can prevent soil erosion and lead to the growth of a soil chemistry supportive of multiple life-forms are highly desirable.

In the agricultural field, the use of algae as a fertilizer has been proposed. U.S. Pat. Nos. 4,879,232 and 4,950,601 to MacDonald et al. and U.S. Pat. No. 4,921,803 to Nohr, each of which is incorporated herein by reference, disclose the use of heterocystous blue-green algae as a fertilizer which fixes nitrogen.

The use of algae to provide a cover crop and to improve soil aggregation has also been proposed. U.S. Pat. No. 4,774,186 to Schaefer Jr. et al., which is incorporated herein by reference, discloses an aqueous suspension comprising water, algae and a carrier which is sprayed on soil. The carrier comprises water dispersible particulates such as fine grain clay, lactose, whey, guar gum, gum arabic, agar or maltodextrin. The algae and the carrier are initially combined to form a dry, flowable mixture. The mixture is then added to water at or near the site of application to form a suspension, which is sprayed onto a field using, e.g., a conventional irrigation system.

A prior attempt at producing cyanobacterial inoculants has focused on the agglomeration of the bacteria into small pellets. These pellets are produced via the filtration of algal blooms grown in bulk within cylindrical tanks of water, with broad spectrum light focused on the tanks. Using such growth methods, the establishment of a sufficiently large quantity of microcoleus in the batch reactor tank has been found to take several weeks to months. This approach is not a viable candidate for large scale, economical production of the cyanobacteria. The process of bulk bacterial growth in water cylinders, while a standard of industry for many bacterial processes, is most likely not natural for the pioneer algae species of the present invention. In arid soil conditions, the cyanobacteria grow in a certain ratio of water, sunlight and air, where there is very little water. The water tank approach has been found to be incompatible with this preferred growth mode. This prior attempt at the pelletization process has also been found to be limiting in the ability to produce viable organisms in an arid environment. Due to the fibrous nature of microcoleus, they may not have the ability to extricate themselves from a fiber agglomerate. As a result, the yield efficiency of actual regrowth from dormancy has been found to be quite low. In addition, the pellet process requires the use of a grinder to break up the pellets prior to dissemination. As a result, the cyanobacteria suffers a high mortality in the mechanical crushing that takes place in the grinder, which severely reduces the efficiency of the pellets.

Despite the above-noted efforts, a need still exists for an effective and cost efficient method of reclaiming land using cyanobacterial inoculants.

SUMMARY OF THE INVENTION

One aspect of the present invention provides an economical method of applying dormant cyanobacterial inoculants to the surface of disturbed land such as arid soil. The method preferably utilizes live, naturally occurring, filamentous, terrestrial cyanobacteria such as Microcoleus vaginatus. The inoculant preferably has a viable shelf life of at least one year. Furthermore, the application of the inoculant preferably does not require water, and may use a dissemination apparatus such as broadcasting equipment, rangeland drilling equipment, aircraft dispersion equipment or the like.

An object of the present invention is to provide a method of reclaiming soil. The method includes the steps of inoculating a substrate material with cyanobacteria, and disseminating the inoculated substrate material on soil, whereby at least a portion of the cyanobacteria act to bind particles of the soil together.

Another object of the present invention is to provide a method of inoculating a substrate material with soil-binding cyanobacteria. The method includes the steps of growing cyanobacteria in a thin-film growth medium, and inoculating a substrate material with the cyanobacteria.

A further object of the present invention is to provide a material for reclaiming soil. The material comprises a substrate material, and cyanobacteria inoculated on the substrate material.

These and other objects of the present invention will be more apparent from the following description.

DETAILED DESCRIPTION

Figure 1:
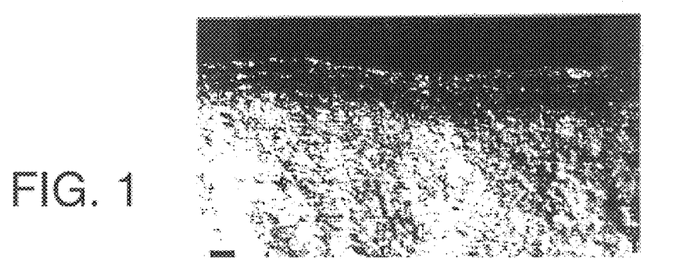
FIG. 1 is a photomicrograph showing a mat of filamentous cyanobacteria formed on a soil surface.

Cryptogamic crusts formed in accordance with the present invention benefit the soils on which they grow in a variety of ways, including the mechanical stabilization of surface soil and consequent reduction of soil erosion. Soil algae, particularly filamentous cyanobacteria, form a mat on the soil surface during times of moist, moderate weather. This mat consolidates the soil under it, as shown in the cross-section soil micrograph of FIG. 1. The cyanobacteria perform the task of soil stabilization. They remain dormant until the proper combination of sunlight and water present themselves and, in their non-dormant phase, produce a fibrous mucilage having a skeletal byproduct which assists in binding the soil together.

Figure 2:
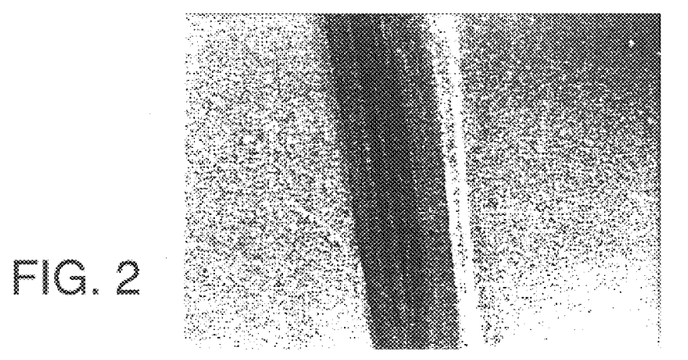
FIGS. 2–4 are photomicrographs showing examples of cyanobacteria which may be used in accordance with embodiments of the present invention.
Figure 3:
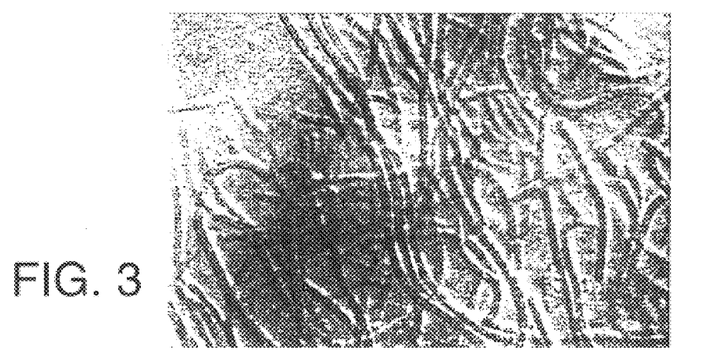
Figure 4:
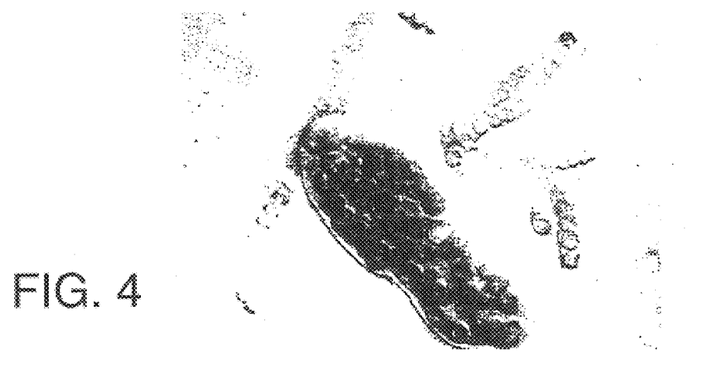

In accordance with the present invention, the term "cyanobacteria" is defined broadly and includes any type of algae capable of binding soil particles together. Preferred genera of filamentous cyanobacteria used in accordance with the present invention include Microcoleus, Nostoc, Schizothrix, Phormidium, Plectonema, Totypothrix, Leptolyngoya, Oscillatoria and Scytonema, some of which are shown in FIGS. 2–4. FIG. 2 is a photomicrograph of Microcoleus vaginatus. FIG. 3 is a photomicrograph of Schizothrix calciola. FIG. 4 is a photomicrograph of Nostoc puntiferme. Any other suitable cyanobacteria which adequately bond soil particles together may be used in accordance with the present invention.

Figure 5:
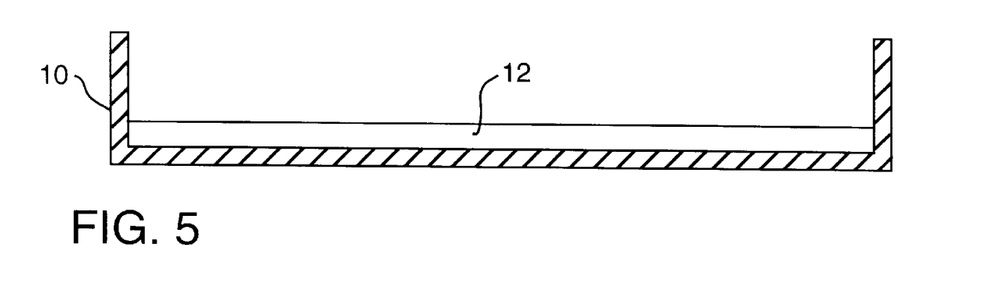
FIGS. 5 and 6 are partially schematic illustrations of thin-film cyanobacteria growth methods in accordance with embodiments of the present invention.
Figure 6:
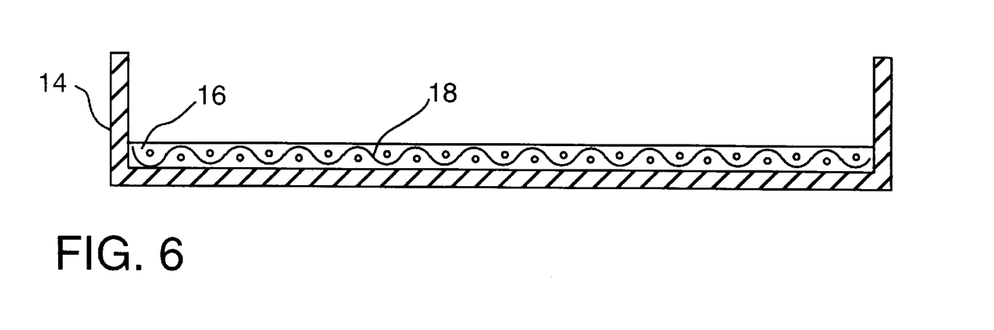

In accordance with a preferred embodiment of the present invention, the growth of microcoleus is accomplished in shallow trays or the like, providing sufficient water to initiate and sustain a thin film growth of the cyanobacteria. FIGS. 5 and 6 schematically illustrate such a thin film growth process. In the embodiment shown in FIG. 5, the cyanobacteria is grown in a container 10 in a shallow liquid medium 12 such as water, without the use of a substrate material other than the container surface 10 to support the algae. In the embodiment shown in FIG. 6, the cyanobacteria is grown in a container 14 in a similar shallow liquid medium 16.

In accordance with the thin-film growth method of the present invention, the thickness of the liquid growth media 12 and 16 shown in FIGS. 5 and 6 is preferably less than about 5 mm.

In the embodiment of FIG. 6, a substrate material 18 is provided in the liquid medium 16 in order to facilitate the growth of the cyanobacteria. In a preferred embodiment, the substrate material 18 is sprayed with the liquid medium periodically in order to keep the substrate moist during the growth process. The substrate material 18 may be the same material upon which the cyanobacteria are supported during subsequent field dissemination, or may be different from the final support material.

In accordance with the present invention, the thin film growth process has been found to be a highly improved method of mass producing cyanobacteria. It is a commercially viable technique that works with various species, such as Microcoleus vaginatus, Schizothrnx calcicola, Nostoc and the like. The thin-film method provides reduced production time and a significantly lower amount of water consumption in comparison with prior pelletization techniques. Table 1 summarizes this comparison.

TABLE 1

Comparison of Pelletization and Direct Growth Process Parameters

| Process Parameter | Pelletization | Direct Growth |
|---|---|---|
| Time to process inoculant from isolated species | 4–5 months | 6–8 weeks |
| Quantity of isolated species needed for field test | 250 liters | 3 liters |
| Time needed to grow inoculant for field test | 2–3 months | 5–10 days |

When inoculation of an area is planned, the preferred initial step is to identify naturally occurring cyanobacteria species present in the intended area. Once identified or isolated, a starter batch of the bacteria is preferably grown to produce the cyanobacteria which will be applied to the substrate material for inoculation. The process parameter "time to process inoculant from isolated species" set forth in Table 1 describes the time period between isolation or identification of the naturally occurring species and producing the starter batch. Because a smaller quantity of cyanobacteria is required, the production time is less. In the preferred embodiment, the cyanobacteria cultures are initially grown in water. The process parameter "quantity of isolated species needed for field test" set forth in Table 1 describes the quantity (liters) of cyanobacteria culture that are required for a field test. In accordance with a preferred embodiment of the present invention, direct growth of cyanobacteria on a substrate is a much faster method of producing cyanobacteria than pelletization methods. The process parameter "time needed to grow inoculant for field test" in Table 1 provides a direct comparison of the time required to produce inoculant by the present direct growth method versus the time required to produce pelletized cyanobacteria.

The preferred thin film growth method of the present invention demonstrates a marked acceleration in the growth of microcoleus. The algal concentrate can be applied to a variety of particle substrates using spray drying techniques. In addition to particle supports for the spray dried bacteria, the spray dried medium may be applied to biodegradable fabrics and the like. Spray drying is preferably performed at air temperatures that are sufficient to accelerate the drying process, but not kill the cyanobacteria. Such an approach permits the storage of dormant microcoleus on, for example, rolled up mats that can be disseminated using suitable broadcasting hardware.

Direct growth of microcoleus onto a biocompatible/biodegradable fabric as a single processing step, as shown in FIG. 6, may be performed in accordance with a preferred embodiment of the invention. The fabric, after establishing a viable algal colony, is then preferably air or vacuum dried in a manner so as not to damage or kill the algae, and is then collected onto a spool or other support for storage. The spooled fabric is then disseminated in a suitable manner, as more fully discussed below.

To assist in anchoring the algae, various types of substrates may be provided on which the organisms can grow and attach themselves. The substrate materials should preferably have characteristics such as biocompatibility, environmental compatibility, porosity and suitable physical parameters. The term "substrate material" as used herein means any material which may be inoculated with the cyanobacteria, which is capable of supporting the cyanobacteria in a substantially dormant state, and which may be disseminated on the ground. Substrate materials capable of providing biodegradability over a long duration, e.g., several months to years, preferably include natural fiber materials such as hemp, cotton, cellulose, jute or coconut fiber woven cloth, as well as organic polymer fibers. The organism is provided on a stable substrate in such a manner that it can more easily migrate and will be disseminated with little possibility of mechanically induced mortality. Further, the microcoleus may prefer the mobility permitted within the weave of a fabric for ease of attachment. If the algae is predominantly located on one side of the fabric which happens to be face down due to the randomness of dissemination, upon activation by rain, the organism will be able to easily migrate through the fabric weave toward the sunlight. Alternatively, the substrate material may comprise non-woven fabrics.

Hemp (04-H1-43) and hemp/cotton (04-HC46) fabric produce favorable better results. Unsatisfactory growth occurs on certain papers, and is likely due to low pH and possibly chemical residues. Among the fabrics, which were mostly natural, water holding capacity and density of weave were significant factors. Burlap and cheesecloth are coarse weave materials that hold water poorly and may have relatively poor growth results. Hemp and hemp/cotton samples have neutral pH, no added commercial residues and hold water well. These factors in combination are likely responsible for the improved growth noted on these substrates.

As noted previously, the cyanobacteria provided in accordance with the present invention form a mucilage of polysaccharides creating a cryptogamic crust or mat that tends to bind soil particles together and retard erosion. When there is little moisture, the cyanobacteria desiccate entering a dormant stage and then rehydrate, becoming active again when moisture is available. By drying the inoculated substrate we foster a dormancy stage similar to the natural sequence. We lessen cyanobacteria mortality by simulating the natural life cycle of dormancy and rehydration to help the cyanobacteria survive dissemination better and return to an active stage.

Figure 7:
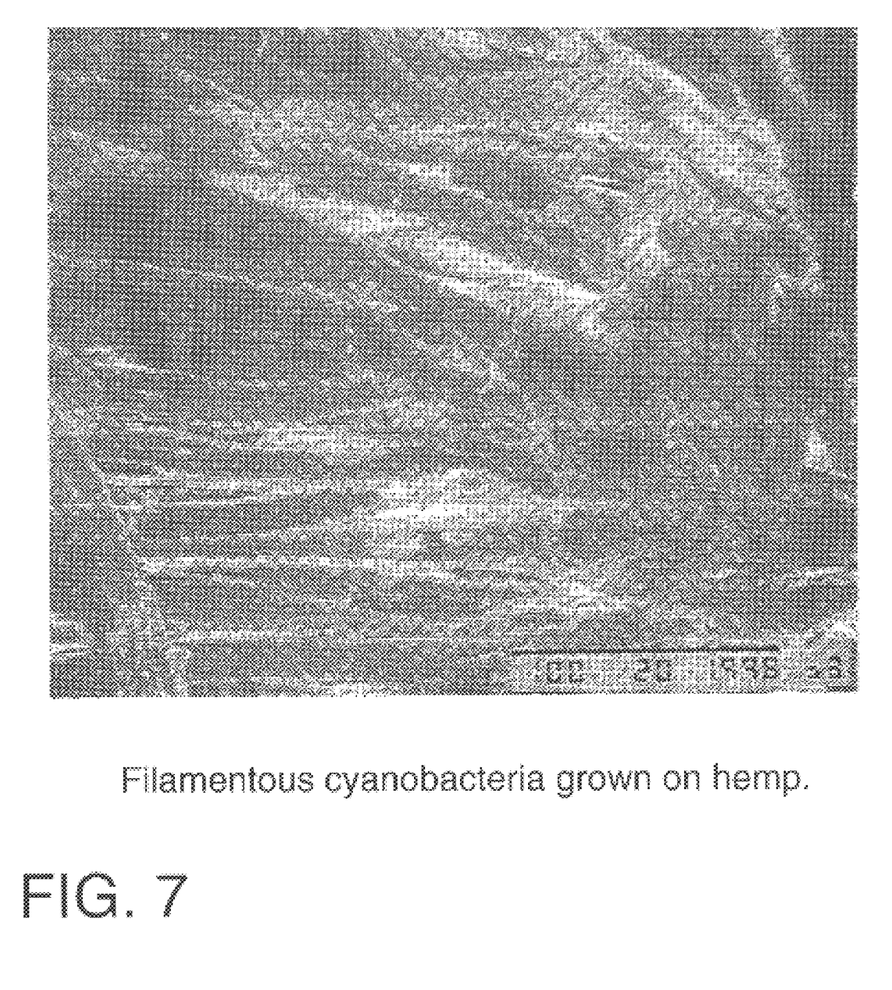
FIG. 7 is a photomicrograph showing filamentous cyanobacteria on a fabric substrate in accordance with an embodiment of the present invention.
Figure 8:
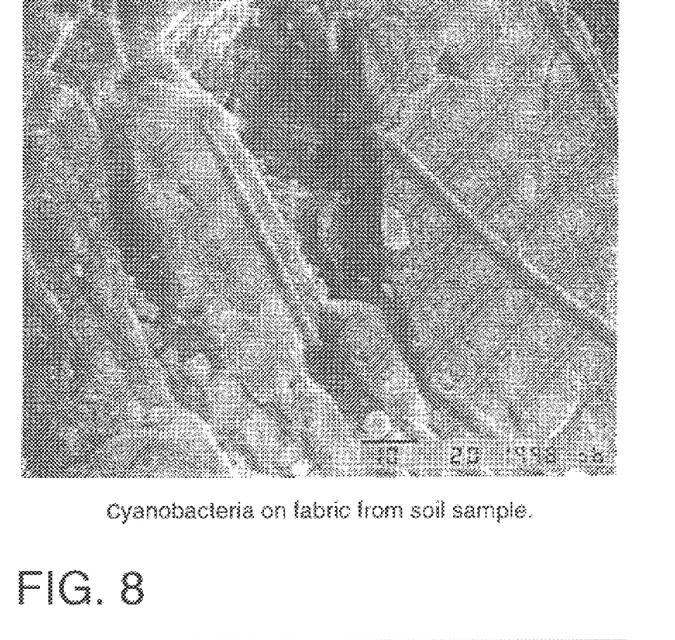
FIGS. 8 and 9 are photomicrographs showing filamentous cyanobacteria on sand particles in accordance with an embodiment of the present invention.
Figure 9:
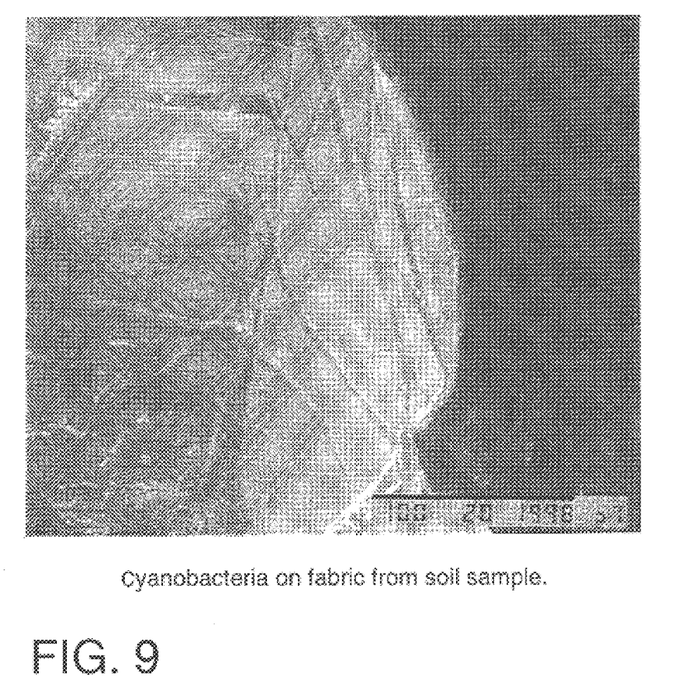
Figure 10:
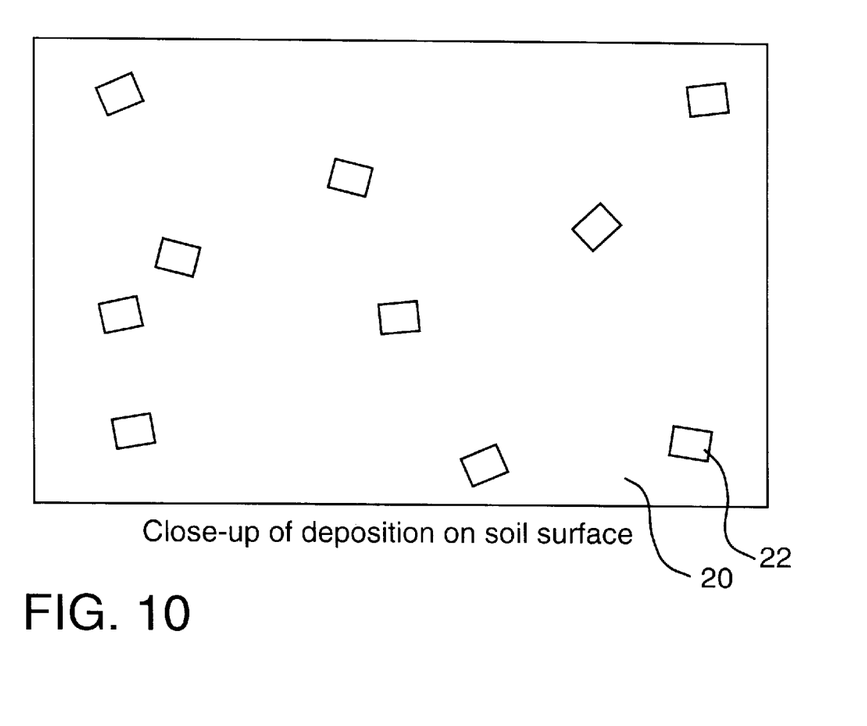
FIG. 10 is a plan view illustrating cyanobacterial inoculant that has been disseminated on a soil surface in accordance with an embodiment of the present invention.

FIG. 7 is a magnification of a fabric sample showing filamentous cyanobacterial interwoven with the fabric. FIGS. 9 and 10 are photomicrographs of cyanobacteria on a sand particle which has attached to the fabric sample. The bottom right corner of each photomicrograph indicates a scale of 10 microns or 100 microns.

Cyanobacteria responds well to spray application and drying. Moisture placed on the dried substrate reactivates the cyanobacteria causing it to spread. Cyanobacteria migrate readily from the substrate to the surrounding soil. Growth levels obtained in this manner over 9 to 10 days equal the levels obtained with pelletized cyanobacteria in five weeks.

Another aspect of producing a viable organism for growth on arid soils is the attachment/adhesion of the dormant species to the intended location. If fine powders or pellets of inoculant are disseminated over large areas prior to seasonal rains, wind will transport the particles over potentially large distances, as it does the eroding soil. This windborne transport once again lowers the efficiency of the inoculant, since there is no way of determining where the materials will ultimately be deposited. For this reason, the substrate used in accordance with the present invention is preferably of sufficient size to insure rapid fallout from the dissemination stream and to resist wind erosion.

In accordance with the present invention, the shape and size of the inoculant substrate materials are preferably selected in order to substantially reduce or prevent wind erosion of the material. The pieces of substrate material may be square, round or any other suitable shape. The inoculant pieces are preferably substantially flat, having thicknesses of from about 0.1 to about 5 mm, more preferably from about 0.5 to about 1 mm. Such substantially flat pieces typically have a length of from about 1 to about 50 mm, and a width of from about 1 to about 50 mm. For example, where square inoculant pieces are used, the length and width of such pieces are preferably from about 5 to about 10 mm.

FIG. 10 is a plan view showing inoculant material pieces 20 disseminated on a soil surface 22. As used herein, the term "dissemination" means the distribution of multiple pieces of the inoculated substrate material on the soil. The pieces of inoculated substrate material may rest on the surface of the ground, or may be located a short distance under the surface of the ground. After dissemination, the inoculated substrate material preferably covers from about 1 to about 90 percent of the soil surface, more preferably from about 2 to about 50 percent.

In a preferred embodiment, the substrate may include an adhesive in order to assist in the retention of the pieces of inoculant material in the desired location. For example, the adhesive may be a shelf-stable, biocompatible organic polymer adhesive that will, under ultraviolet light, degrade into a tacky adhesive and bind with surrounding soil particles. This binding process effectively makes the inoculant heavier, increasing its resistance to wind erosion as it awaits naturally occurring rains to activate its algal coating.

In accordance with a preferred embodiment of the present invention, the large area seeding of soil acreage with the cyanobacterial inoculants includes a bulk material dissemination or dusting system. This function may be satisfied through the use of modified military obscuration systems, agricultural sprayers, rangeland drill equipment, aerial dissemination systems, or the like. The dissemination systems preferably include components for the storage of a densified form of the material, mechanical feed rate control and transport, deagglomeration, pneumatic transport and dissemination.

Figure 11:
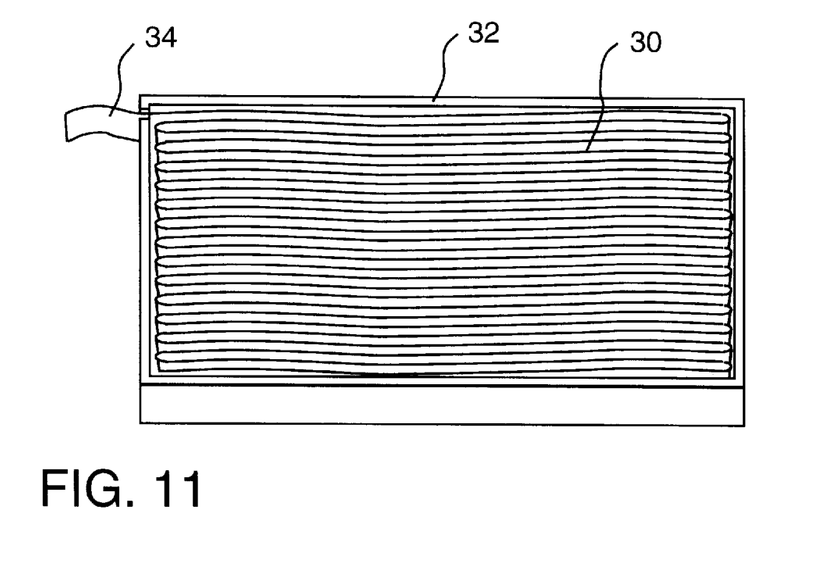
FIG. 11 is an isometric view of a cyanobacterial inoculant material in the form of a continuous belt in accordance with an embodiment of the present invention.

FIG. 11 illustrates a cyanobacterial inoculant substrate material that is provided in the form of a continuous belt 30. The continuous belt 30 is folded in a box 32, and may be fed through an opening 34 in the box 32. The continuous belt 30 may be fed from the box 32 into a self-contained broadcast dissemination unit, as more fully described below. This packaging approach provides sealed encapsulation, preventing moisture intrusion for long term storage.

The continuous belt 30 may be an uninterrupted length of woven material or a belt structure having multiple individual packing cells along its length. The width and length of the continuous belt 30 are of such dimensions as to provide adjacent cells along the belt length and to hold the cells within the belt width. The cells are spaced apart by partitions which extend across the belt width between the cells. A zipper seal which may extend along the belt length is fixed between the cells and a belt edge on at least one side of the belt. The cells may contain cyanobacteria inoculant which is sealed inside of the cells.

The dimensions of the continuous belt 30 are limited by the cutter size of the dissemination apparatus. The cutter may be any mechanism which chops through the woven material or shreds the individual cells holding the inoculant and may include rotary or chopping mechanisms. The continuous belt 30 length may be any convenient continuous length. The belt width permits the alignment of adjacent cells along the belt length in a single uniform row and may also include parallel rows. Preferably the belt width is from about 1 inch to about 4 inches, and more preferably from about 2 inches to about 2.5 inches. Larger belts may be used, if desired. The continuous belt 30 is constructed of any material that is an acceptable growth media for cyanobacteria, or which will enclosed cyanobacteria inoculant in multiple individual packaging cells and which allows the belt to be shredded or chopped in the dissemination apparatus. Preferably, the continuous belt 30 is a plastic or natural fiber construction, and most preferably the belt is polyethylene or hemp.

The continuous belt 30 may be placed in a container or on a spool. When the belt is packaged in a container, such as the box 32 shown in FIG. 11, the belt width is limited by the container width. Preferably, the belt is layered in the container which is a rectangular box, more preferably the belt is layered in a cardboard rectangular box. The belt is easily accessed from the box 32, with the box conveniently placed inside a storage magazine (not shown) as part of the dissemination apparatus which allows the belt to be loaded into the dissemination apparatus. For example, the box 32 may have rectangular dimensions of 10.5 inches in height, 21 inches long, and 2.8 inches wide, with an approximate volume of 500 in$^3$ (8193.5 cm$^3$).

The belt 30 as shown in FIG. 11 may be drawn into a multiblade chopper mechanism where the belt packaging is cut, for example, into ¼ inch slices, releasing the pieces of inoculated material. This method of deagglomeration is substantially less stressful on the material than crushers, pulverizers or pin mill grinders and preserves the viability of the cyanobacterial inoculants. The loose inoculated material may be entrained into an air ejector or other apparatus for dispersion. The broadcast system may project the loose material into the ambient environment, resulting in deposition of material on the surface of the ground.

A compact portable system capable of disseminating both solid particulates and fibrous aerosol material may be used. In one embodiment, a unique belt-form packaging approach common to both the fine particulate and continuous fiber weave may allow both materials to be processed and aerosolized with the same apparatus. For example, the dissemination unit may include a digital speed control which allows the operator to set the continuous belt feed rate. The system may require only a compressed air source and small amount of electrical power.

In accordance with another embodiment of the present invention, the inoculant carrier materials may also be disseminated using agricultural dusters, for example, dusters manufactured by Buffalo Turbine of Gowanda, N.Y. The Buffalo Turbine sprayers are available in sizes ranging from hand carried units, back-pack blower units, up to trailer towed sprayers. For instance, the Model D is a complete, stand-alone, self-contained system including a solid material hopper, drive motor, axial fan and ejection duct, which weighs about 600 pounds and will fit onto the bed of a ½-ton pick-up truck or HMMWV. The Model D is powered by a 9.2 hp gas engine and is capable of disseminating solid materials at rates up to 25 lb/min. The large axial fan develops 3500 cfm of air flow.

The inoculant materials of the present invention may also be disseminated with rangeland drill equipment. In this embodiment, the pieces of inoculant material are preferably placed a minimal distance into the soil to permit sufficient access to sunlight. Rangeland drilling techniques may therefore be adapted in accordance with the present invention to include the deposition of inoculant fabric strips or the like.

The following examples illustrate various aspects of the present invention, and are not intended to limit the scope thereof.

A variety of fabrics, papers, and plastic substrates were tested for their water holding capacity and ability to withstand sterilization by autoclaving. A subset of these substrates were tested for their ability to support growth of the cyanobacterium Microcoleus vaginatus. Loss in viability of M. vaginatus immediately following dehydration on the best substrates (hemp and hemp/cotton blend) was measured. Viability and growth rate of M. vaginatus was tested on a sand substrate, with uninoculated sand and liquid M. Vaginatus treatments used for comparison. Two additional strains, Schizothrix calciola and Nostoc species, were tested for their ability to grow on 100% hemp natural fabric.

A growth model was established using an open weave or porous substrate as a simulated crust for controlled production of cyanobacteria in a laboratory environment. A total of 13 different substrate materials were selected for initial evaluation because of their low cost, natural or biodegradable material, and their coarse or open weave characteristics. Water holding capacity was tested by cutting a 15 cm$^2$ piece of each fabric, lowering it into a 10 ml graduated cylinder filled with 10 ml water, removing it from the water with tweezers, and allowing all water to drip back into the cylinder. The water removed by the substrate which did not drip back into the cylinder was calculated by subtraction. The most absorbent substrates were the fabrics, with hemp and hemp/cotton blends generally having higher absorbencies than the cotton cheesecloth. Water absorbency may be an important characteristic of the substrate, since both ability to stay moist during culture and length of time to dry out are influenced by this trait.

Substrate material samples were sprayed with Microcoleus vaginatus and placed in shallow trays. Material samples were sprayed with water daily to prevent drying. Each material sample was replicated three times and tests to detect the presence of chlorophyll a using the DMSO method were conducted over 13 days. Natural 100% hemp and hemp/cotton fabric produced substantially greater cyanobacteria growth than the other substrate materials.

Viability tests were performed to evaluate three different application/drying/rehydration sequences to determine which sequence resulted in the least cyanobacteria mortality and the best growth rates after rehydration. Strips of 100% hemp and hemp/cotton were sprayed with cyanobacteria and hung to dry overnight. The samples were air dried at room temperature with no mechanical acceleration of the drying process. Three replicates were prepared for each fabric and subsamples were taken to test for chlorophyll a. After the initial drying, the fabric samples were submerged in Z-8 growth media (Carmichael, 1986) to rehydrate. Additional chlorophyll a samples were taken 2 days later showing appreciable mortality in both fabrics.

A second viability test was started using five replicates for each fabric. After the initial drying, the fabric samples were rehydrated by moistening instead of being submerged. Still, the cyanobacteria mortality was not acceptable.

Figure 12:
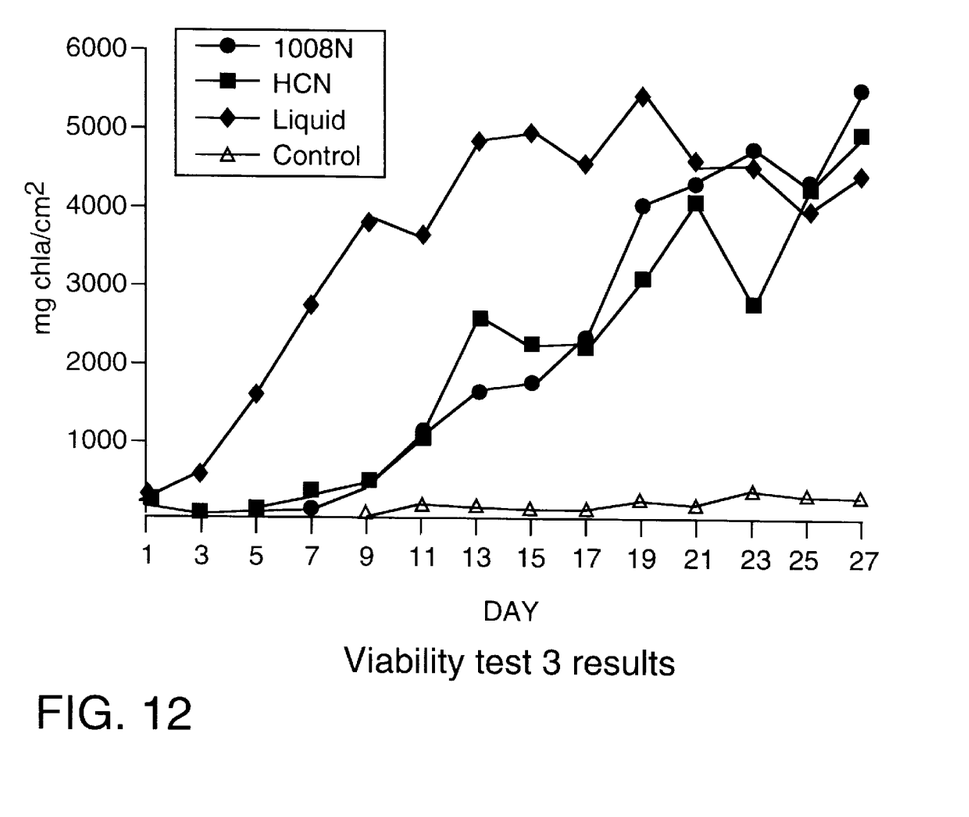
FIG. 12 is a graph illustrating cyanobacteria viability test results in accordance with an embodiment of the present invention.

A third viability test was performed. Cyanobacteria was applied to the fabric at a rate of 0.03 g/in$^2$ and grown for 2 days. The fabric was kept moist during the 2 day growth period and then dried for 48 hours. After drying, the material was chopped into roughly ¼-inch fragments. Chopped material was applied to sterilized play sand. For comparison, cyanobacteria was applied in liquid culture directly to sterilized play sand with no fabric. Cyanobacteria growth started faster on the plots receiving liquid cyanobacterial amendment, and consequently maintained higher densities until day 21. Both fabrics gave very similar growth, with hemp/cotton having slightly higher densities initially, but 100% hemp having higher densities later in the experiment, as shown in FIG. 12. The control (no amendments) had very low concentrations due to the presence of some green algal contaminants. There were no cyanobacterial contaminants on the control trays, nor were there any green algal contaminants in any of the amended trays.

All growth seen in amended treatments was due to the inoculants rather than contamination. At the conclusion of the experiment the fabric-based amendments had cyanobacterial densities equal to or greater than the liquid culture amendments, as shown in FIG. 12. Multifactor ANOVA showed that overall differences in growth means were highly significant, with significant interaction due to the fact that the liquid amendment showed greater early growth. This example shows that cyanobacteria survive the production and drying process, and that they are able to escape from the fabric pieces to the soil.

The viability tests were a controlled sequence of experiments in which discrete steps were adjusted from one test to another in order to observe the resulting effect on cyanobacteria mortality. Cyanobacteria was applied in the same fashion, spraying, for each test. In the first and second test air drying was accomplished over a 24 hour period that began immediately after spraying. The third test, however, delayed air drying and allowed 48 hours of cyanobacteria growth before drying. The drying time was also extended to 48 hours in test three. Another significant difference is that in test 1, rehydration was accomplished by submerging the material in Z8 growth medium while in tests 2 and 3 rehydration was through moistening the samples with a water spray.

Investigations were conducted to identify shelf-stable, biocompatible organic polymer adhesives that would degrade under ultraviolet light to form a tacky adhesive and bind with surrounding soil particles. Adhesives types considered during the investigations were ultraviolet/thermal cure adhesives, wax, release coated adhesives and static charge adhesives.

Characteristics used to evaluate candidate adhesives included their ability to adhere to hemp or hemp cotton fabric, their ability to provide sufficiently low adhesion under stored conditions to facilitate dissemination of chopped inoculant, toxicity to inoculant species and surrounding soil, and their impact on migration of the cyanobacteria from fabric substrate to soil. Microsphere adhesive and implanted charge adhesive emerged as the most promising candidates for this application.

Microsphere adhesives are a release coated adhesive. They offer minimum surface contact adhesion and are unlikely to impede migration of the cyanobacteria from fabric to soil. Designed for repositioning while maintaining tack, these adhesives provide low adhesion that should not create clumping during dissemination. Additionally, these adhesives will allow the substrate fabric to be stored in roll form, yet be easily unrolled, chopped, and disseminated.

Implanted charge adhesives are a recent development that hold great promise with substantially no chemical effects that could prove toxic to the cyanobacteria or surrounding soil. Opposing electrical charges are placed on opposite sides of treated material offering particle entrapment capabilities similar to a HEPA type filter. The charge does not decay over time and is still effective after water immersion. Since implanted charge technology works on hydrophobic materials, the hemp materials and other water absorbing cellulosic materials may not accept this implanted charge. Hydrophobic materials can however, be readily chopped and added as a composite to a fabric to attain the desired charge agglomeration characteristics.

Tests were devised to evaluate whether microsphere adhesive or implanted charge adhesive improved the ability of chopped substrate material to resist wind erosion or water runoff.

Soil types predominant in the most likely regions to be inoculated are clay loam or silty clay loam. The United States Department of Agriculture Soil Conservation Service defines loam as a mixture of the three basic soil separates, which are sand, silt and clay. Particle sizes and proportion ranges of these components by volume are set forth in Table 2.

TABLE 2

| Type | Particle Size Range | % Composition |
|---|---|---|
| Sand | 0.05 mm–2.0 mm | <52 |
| Silt | 0.002 mm–0.05 mm | 28–50 |
| Clay | <0.002 mm | 7–27 |

A mix was prepared using the three soil separates in the proportions listed above. Mason's sand, commonly used as a constituent when preparing mortar or cement, was used for the sand portion of the soil sample. Average particle size of the sand was 1 mm. Silt is defines by the Soil Conservation Service as a mineral in the particle size range listed previously. Silica with an average particle size of 0.01 mm was used for the silt portion of the mix. China clay with an average particle size of 0.0004 mm (0.4 microns) provided the clay portion of the mix. Proportions for the custom mix were 44% mason's sand, 39% silica and 17% china clay. The initial soil mix was extremely loose and did not have the look or texture of an arid soil. Water equaling 10% of the soil volume was added to help consolidate the mixture and obtain a more realistic form and texture.

A wind tunnel was constructed to perform a wind erosion test. Air flow produced by a 21 inch box fan passed through a contraction to increase the flow velocity. The contraction was connected to a test section and a flow straightener was located at the intersection to smooth the flow and remove turbulence as the air entered the test section. The soil sample tray dropped into a cavity located in the floor test section. The soil tray was a rectangular plastic tray with dimensions of 10 inches wide, 16 inches long and 3 inches deep. A small ramp in front of the tray provided a gradual flow rise to the edge of the tray, preventing a turbulent zone that could result at the leading edge of the tray.

A rotary vane anemometer was used to measure flow velocity through the test section at various fan speed settings. Flow velocities measured were 6.5 mph (low), 7.8 mph (medium) and 8.8 mph (high).

Fabric particles were deposited on the soil sample tray at an application rate of 4 grams/$m^2$. Deposition consisted of dropping individual particles onto the soil from about 4 inches above the surface. Particles were dropped with no preference to which side contacted soil. The distribution was random but uniform, and no particles overlapped or touched one another. FIG. 10 shows a close-up view of the resulting deposition on the soil sample prior to wind erosion testing.

Tests were conducted using chopped fabric with no adhesive to identify the baseline characteristics. Then chopped fabric with adhesive was exposed to the same conditions to identify any improvement that could be directly associated with the adhesive. A total of eleven wind erosion tests were conducted. The detailed results are shown in Table 3. Average results are provided in Table 4. All wind erosion tests were one minute in duration.

TABLE 3

Number of Particles Resuspended in Wind Erosion Tests

| Particle | Fan Speed | |
| --- | --- | --- |
| Type | Medium | High |
| Untreated | 3 (7%) | 7 (16%) |
|  | 5 (12%) | 10 (23%) |
| Microsphere | 0 | 3 (7%) |
| Adhesive | 2 (5%) | 7 (16%) |
| Ion Implantation | 15 (35%) | 25 (58%) |

TABLE 4

Average Resuspension from Wind Erosion

| Particle | Fan Speed | |
| --- | --- | --- |
| Type | Medium | High |
| Untreated | 4 (9%) | 9 (21%) |
| Microsphere Adhesive | 1 (2%) | 5 (12%) |
| Ion Implantation | 15 (35%) | 25 (58%) |

The wind erosion results indicate that microsphere adhesive treated particles tend to resist erosion as compared to untreated particles. It was observed during particle deposition that as fabric particles impacted the soil surface, individual soil particles adhered to the fabric as it tumbled into its resting state. The added weight of soil particles decreased the tendency for the fabric to be set in motion by wind. If a particle was set into motion by the wind, it did not lift into the air stream and become airborne. Instead it tumbled across the surface, and in doing this picked up additional soil particles. In most cases, this accumulation of soil particles caused the fabric to stop and remain on the surface, having moved only a short distance. A particle that did this was not considered resuspended because although it moved, it remained on the soil surface which itself represents a very small area.

Ion implanted particles where more severely resuspended as compared to untreated particles. The problem with these particles may be in the method used to apply the ion implantation. The ion implantation was actually applied to a melt-blown polyethylene, and that the polyethylene was applied to one side of the hemp/cotton substrate. When this laminate was cut into ¼ inch square particles, the edges of the polyethylene typically protruded above the hemp/cotton surface. In the wind tunnel, these protruding edges created considerable air drag causing the particles to be easily blown off of the surface. It is suspected that if the ion implanted fabric was more integrated with the hemp/cotton, the results would be improved.

A garden sprinkler connected to a water faucet was used to simulate rain. The soil sample tray was placed under the falling water droplets and tilted at a 15° angle to simulate run-off. A graduated cylinder placed next to the soil sample was used to determine the rain fall amount and a stop watch was used to time the test duration so that rain fall rate could be calculated. The rain tests are conducted for a duration of 3.5 minutes each. The results are shown in Table 5.

TABLE 5

Number of Particles Washed Away in Rain Erosion Tests

| Sample Type | Rain Fall (inches) | Rain Fall Rate (in./hr.) | # Particles Washed Away |
| --- | --- | --- | --- |
| Untreated | .4 | 6.8 | 0 |
|  | .5 | 8.5 | 0 |
| Microsphere Adhesive | .55 | 9.4 | 0 |

The rain fall rates simulated during testing represented very severe rain conditions. Typically a heavy storm would produce 1 or 2 inches of rain per hour. Even considering this, no particles were washed away in rain testing. When water contacts a hemp/cotton particle, the particle absorbs the water. The soil under the particle absorbs water quickly as well. The water content between the water and particle creates a considerable attractive force due to the polar nature of water and its strong tendency to be attracted to itself. This tendency was sufficient to secure the particles onto the soil surface. A secondary erosion effect further reduced the potential to wash particles away. The presence of a hemp/cotton particle on the soil surface protected the soil under the particle from being eroded by the falling water droplets. Soil regions around the particle, however, were eroded. After a short time, small mounds formed under each particle, with the particle centered on top of the mound. After formation of the mounds, water flowed around and between each mound, further increasing the tendency for erosion to occur only around the particles. The particles were elevated above the run-off and not affected.

These examples indicate that a surface binding treatment reduces the tendency for the preferred soil inoculant to be eroded by wind, and may reduce the tendency for the inoculant to be eroded by rain.

Whereas particular embodiments of this invention have been described above for purposes of illustration, it will be evident to those skilled in the art that numerous variations of this details of the present invention may be made without departing from the invention as defined in the appended claims.

What is claimed is:

1. A method of aggregating soil comprising:
   inoculating a substrate material with cyanobacteria by growing the cyanobacteria directly on the substrate material; and
   disseminating the inoculated substrate material on soil, whereby at least a portion of the cyanobacteria act to bind particles of the soil together to thereby aggregate the soil.

2. The method of claim 1, further comprising growing the cyanobacteria in a growth medium having a thickness of less than about 5 mm.

3. The method of claim 1, further comprising drying the substrate material after the cyanobacteria is grown to cause the cyanobacteria to enter a substanially dormant stage.

4. The method of claim 1, further comprising inoculating the substrate material by initially growing the cyanobacteria separately from the substrate material and then applying and further growing the cyanobacteria on the substrate material.

5. The method of claim 4, further comprising growing the cyanobacteria in a growth medium having a thickness of less than about 5 mm.

6. The method of claim 4, further comprising applying the cyanobacteria to the substrate material by spraying the cyanobacteria on the substrate material.

7. The method of claim 4, further comprising applying the cyanobacteria to the substrate material by dipping the substrate material into a liquid medium comprising the cyanobacteria.

8. The method of claim 4, further comprising drying the substrate material after the cyanobacteria is applied to cause the cyanobacteria to enter a substantially dormant stage.

9. The method of claim 1, wherein the cyanobacteria is substantially dormant when the inoculated substrate material is disseminated on the soil.

10. The method of claim 9, further comprising exposing the disseminated inoculated substrate material to moisture to cause at least a portion of the dormant cyanobacteria to rehydrate and become active.

11. The method of claim 1, further comprising disseminating the inoculated substrate material on the soil by spraying pieces of the inoculated substrate material over the surface of the soil.

12. The method of claim 1, further comprising disseminating the inoculated substrate material on the soil by inserting pieces of the inoculated substrate material under the surface of the soil.

13. The method of claim 1, wherein the disseminated inoculated substrate material covers from about 1 to about 90 percent of the soil surface.

14. The method of claim 1, wherein the substrate material comprises pieces of material having thicknesses of from about 0.1 to about 5 mm, lengths of from about 1 to about 50 mm, and widths of from about 1 to about 50 mm.

15. The method of claim 1, further comprising:

providing the substrate material as a substantially continuous sheet during the inoculation thereof; and comminuting the substantially continuous sheet to produce pieces of inoculated substrate material prior to the dissemination thereof.

16. The method of claim 15; wherein the substantially continuous sheet is comminuted by cutting.

17. The method of claim 1, wherein the substrate material comprises woven fabric.

18. The method of claim 17, wherein the substrate material comprises hemp.

19. The method of claim 1, wherein the cyanobacteria comprises algae selected from at least one of the genera Microcoleus, Nostoc, Schizothrix, Phormidium, Plectonema, Totypothrix, Leptolyngoya, Oscillatoria and Scytonema.

20. The method of claim 1, wherein the cyanobacterial comprises at least one of Microcoleus, Nostoc and Schizothrix.

21. The method of claim 1, wherein the soil comprises sand.

* * * * *

UNITED STATES PATENT AND TRADEMARK OFFICE
CERTIFICATE OF CORRECTION

PATENT NO.    : 6,228,136 B1
DATED         : May 8, 2001
INVENTOR(S)   : Michael A. Riley et al.

It is certified that error appears in the above-identified patent and that said Letters Patent is hereby corrected as shown below:

<u>Column 3,</u>
Line 10, "Totypothrix" should read -- Tolypothrix --.

<u>Column 8,</u>
Line 48, "1/4—inch" should read -- 1/4-inch --.

<u>Column 11,</u>
Table 3, in column titled "Untreated", second line, place "5 (12%)" under row entitled "Medium". Place "10 (23%)" under row entitled "High".

<u>Column 14,</u>
Line 18, "Totypothrix" should read -- Tolypothrix --.

Signed and Sealed this

Eighteenth Day of June, 2002

*Attest:*

JAMES E. ROGAN
*Attesting Officer*     Director of the United States Patent and Trademark Office